US00PP34169P2

(12) United States Plant Patent
Couturieux

(10) Patent No.: US PP34,169 P2
(45) Date of Patent: Apr. 26, 2022

(54) ***HYDRANGEA* PLANT NAMED 'COUFLORI'**

(50) Latin Name: *Hydrangea paniculata*
Varietal Denomination: COUFLORI

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 0 days.

(21) Appl. No.: 17/527,941

(22) Filed: Nov. 16, 2021

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Weatherly IP Solutions, LLC; Barbara Campbell

(57) ABSTRACT

A new *Hydrangea* plant particularly distinguished by having white flowers tinged with red-purple, and having and obovate plant shape with a broad-spreading habit, is disclosed.

3 Drawing Sheets

Genus and species: *Hydrangea paniculata.*
Variety denomination: 'COUFLORI'.

BACKGROUND OF THE NEW PLANT

The present invention comprises a new and distinct variety of *Hydrangea* plant, botanically known as *Hydrangea paniculata*, and hereinafter referred to by the variety name 'COUFLORI'. 'COUFLORI' originated from an open pollination in France between two un-named and unknown *Hydrangea paniculata* parents. Seeds from the open-pollination were taken from the female parent and sown and a single plant was chosen in March 2013.

'COUFLORI' was first propagated in July 2015 in France. 'COUFLORI' was found to reproduce true to type in successive generations of asexual propagation via softwood cuttings.

SUMMARY

The following are the most outstanding and distinguishing characteristics of this new variety when grown under normal horticultural practices in Boskoop, The Netherlands.

1. White flowers tinged with red-purple; and
2. Having and obovate plant shape with a broad-spreading habit.

DESCRIPTION OF THE PHOTOGRAPHS

This new *Hydrangea* plant is illustrated by the accompanying photographs which shows the plant's overall plant habit including form, and foliage. Photos were taken in August 2021 in Boskoop, The Netherlands. The colors shown are as true as can be reasonably obtained by conventional photographic procedures.

DESCRIPTION OF THE NEW VARIETY

Figure 1:
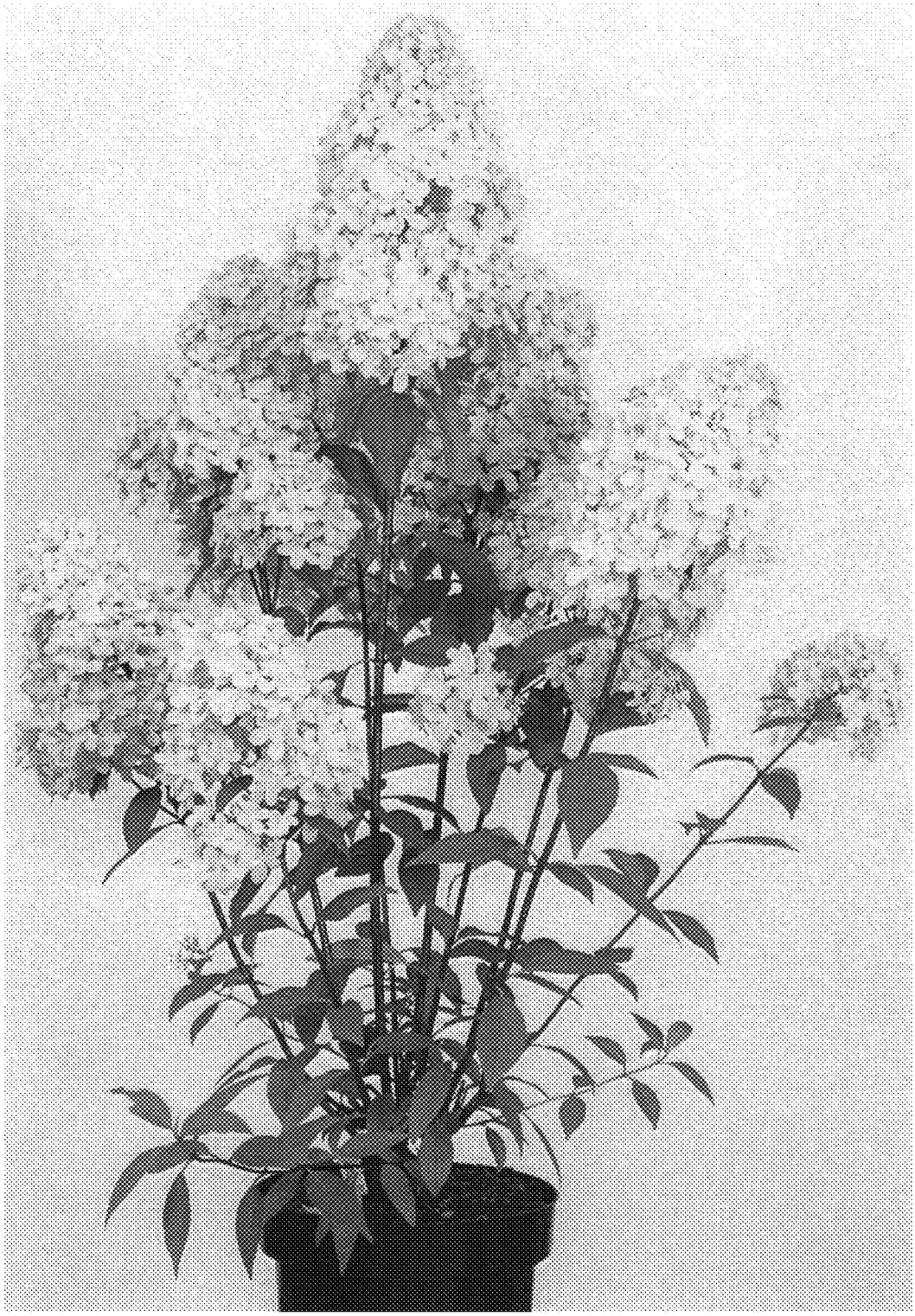
FIG. 1 shows the overall plant habit of 'COUFLORI', including flowers, and foliage.
Figure 2:
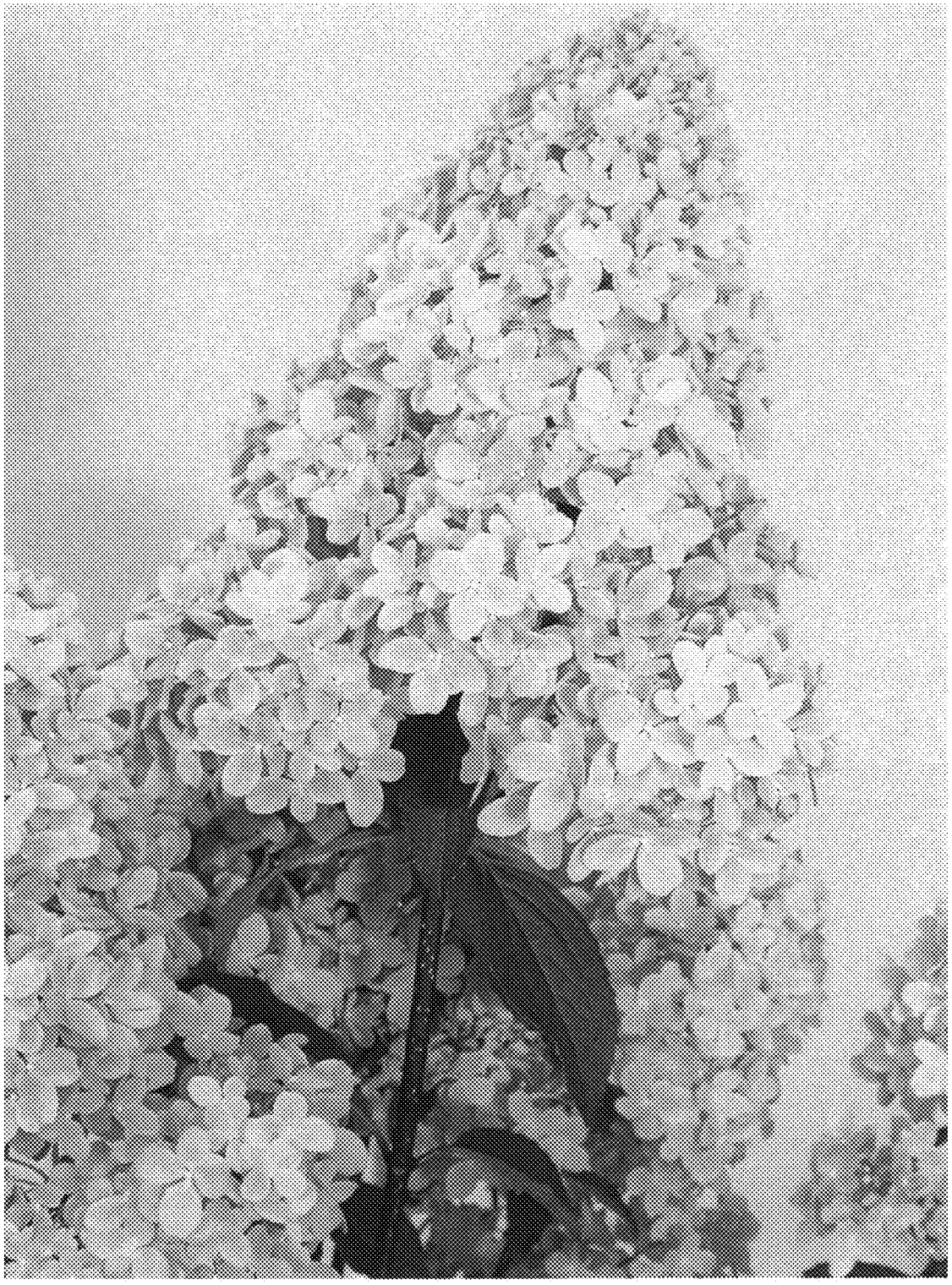
FIG. 2 shows a close-up of the flowers.
Figure 3:
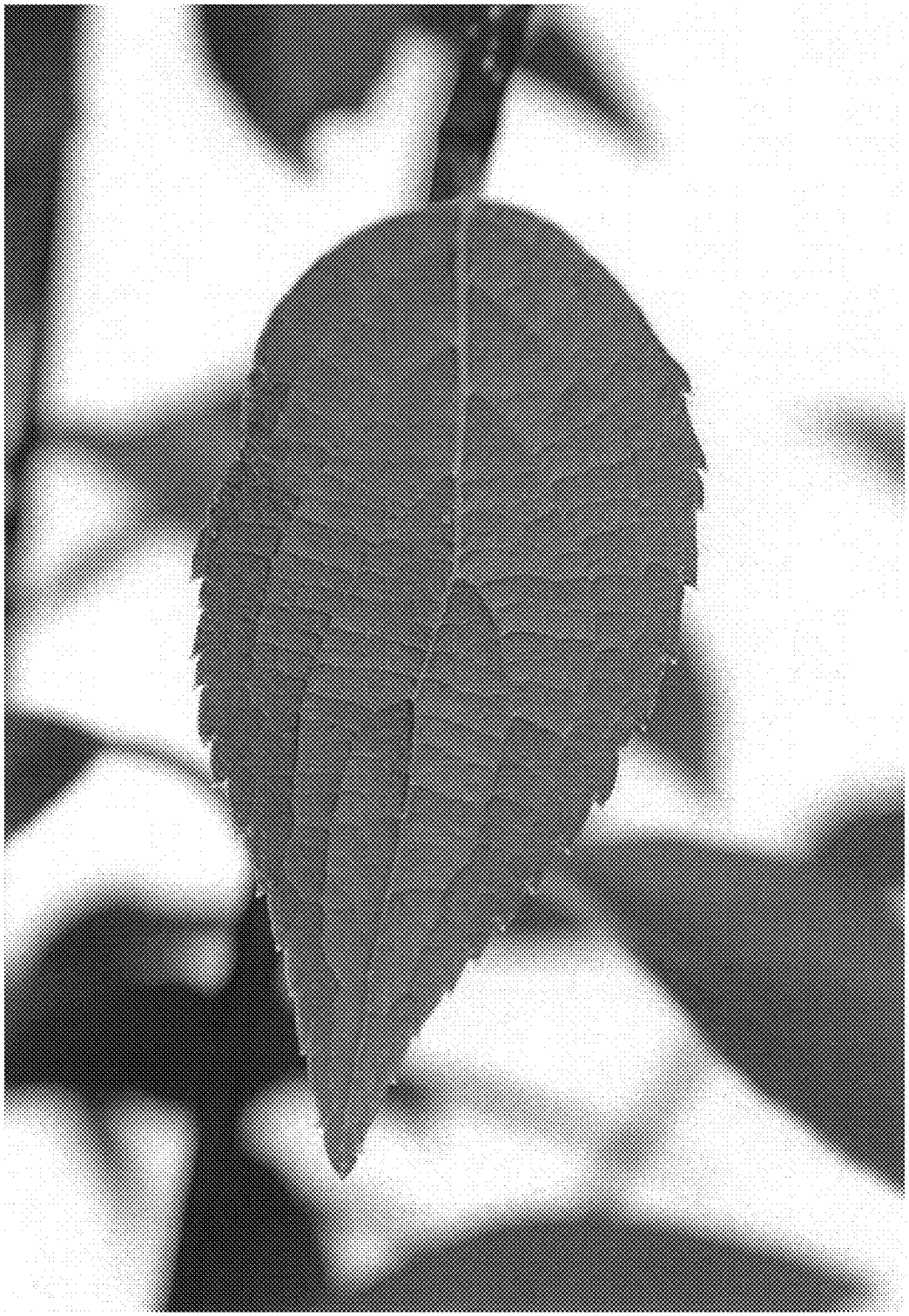
FIG. 3 shows a close-up of an individual leaf.

The following detailed descriptions set forth the distinctive characteristics of 'COUFLORI'. The data which define these characteristics were collected from asexual reproductions carried out in Boskoop, The Netherlands. Data was collected on two-year old plants grown outdoors in a 19 cm circular pot The Netherlands in August 2021. The range of day temperatures was 16° C. to 26° C. and the range of night temperatures was 8° C. to 20° C. Color references are to The R.H.S. Colour Chart of The Royal Horticultural Society of London (R.H.S.), 6$^{th}$ edition (2015).

Classification:

*Family.*—Hydrangeaceae.
*Botanical.*—*Hydrangea paniculata.*
*Common.*—*Hydrangea.*
*Designation.*—'COUFLORFI'.

Plant:

*Propagation type.*—Softwood.
*Time to produce a finished plant.*—Average is one year from propagation to a small finished plant.
*Plant shape.*—Obovate.
*Growth habit.*—Broad spreading upright.
*Average plant height.*—86.0 cm.
*Average plant diameter.*—63.8 cm.
*Growth rate.*—Moderate.
*Vigor.*—Moderate to high.
*High temperature tolerance.*—At least tolerant to USDA Zone 9.
*Low temperature tolerance.*—At least tolerant to USDA Zone 5.
*Weather tolerances.*—Moderate tolerance to wind; moderate to high tolerance to rain.
*Disease/pest resistance and susceptibility.*—Not more susceptible to pests and diseases than other varieties of same species.

Branches:

*Habit.*—Freely branching.

*Basal branching.*—Present.

*Pinching.*—Not required but will improve branching.

*Lateral branches.*—Number of lateral branches per plant: Average of 14. Length: Average is 41.0 cm, excluding inflorescence. Diameter: Average is 0.55 cm. Internode length: Average is 8.5 cm. Appearance and shape: Rounded. Aspect/angle: Spreading-upright; average angle of 37.5 degrees to main branch. Strength: Strong. Color, immature: RHS 183D (Greyed-Purple) and the underside is RHS 182C (Greyed-Red). Color, mature: RHS 200C (Brown) and RHS 200D (Brown); the older bark is RHS N199A (Grey-Brown) and RHS N199B (Grey-Brown). Pubescence: Young stems are sparsely covered with short adpressed hairs; length is 0.5 mm and white (hairs are too small and sparse to be accurately color with an RHS designation). Lenticels: General: Stems are moderately covered with lenticels; lenticels are not visible on mature stems. Length: 2.0 mm. Width: 1.0 mm. Color: RHS 164B (Greyed-Orange).

Foliage:

*Arrangement.*—Opposite or in whorls of 3.

*Number of leaves per lateral branch.*—Approximately 16.

*Shape.*—Ovate.

*Apex.*—Apiculate.

*Base.*—Acute.

*Margin.*—Serrate.

*Length.*—Average is 7.5 cm.

*Width.*—Average is 3.5 cm.

*Texture.*—Upper surface: Smooth but sparsely to moderately pubescent with very short strigose hairs; length is 0.4 mm and colored greyed-white (hairs are too small to be accurately color with an RHS designation). Lower surface: Smooth but moderately pubescent on main and secondary veins with very short adpressed hairs; length is 0.5 mm and colored green-white (hairs are too small to be accurately color with an RHS designation).

*Venation pattern.*—Pinnate.

*Venation color.*—Upper surface: RHS 145A (Yellow-Green). Lower surface: RHS 147C (Yellow-Green).

*Color.*—Immature: Upper surface: RHS 143A (Green). Lower surface: RHS 138B (Green). Mature: Upper surface: RHS 137B (Green). Lower surface: A blend of RHS 138B (Green) and RHS 191B (Greyed-Green).

*Petiole.*—Length: Average is 1.3 cm. Diameter: Average is 1.75 mm. Color: The upper surface is RHS 178B (Greyed-Red) and the lower surface is RHS 199B (Grey-Brown) and slightly tinged with RHS 176B (Greyed-Orange) Appearance and texture: Upper surface is slightly glossy but sparsely covered with very short adpressed strigose hairs that are about 0.3 mm in length and white in color (but too small to be measured with RHS color chart); the lower surface is slightly glossy but sparsely covered with very short adpressed strigose hairs that are about 0.4 mm in length and white in color (but too small to be measured with RHS color chart).

Flowers:

*Natural flowering season.*—Mid-summer to late summer.

*Time to produce a flowering plant.*—One season.

*Fragrance.*—Very faint, sweet and pleasant.

*General.*—Center region of fertile florets surrounded by an outer ring of sterile florets; panicle is 24.6 cm in height and 21.4 cm in diameter and is irregular-conical in shape.

*Peduncle.*—Length: 21.7 cm. Diameter: 0.35 cm. Angle: For the main peduncle, 0 degrees; for lateral peduncles, 40 degrees to the main peduncle. Strength: Moderately strong. Texture: Sparsely covered with thin adpressed hairs; length of hairs is 0.4 mm and too small to be measured with an RHS color chart. Appearance: Matte. Color: RHS 183C (Greyed-Purple) and sparsely to moderately covered with lenticels that are 1.0 mm in length, 0.5 mm in diameter, and RHS 157A (Green-White).

*Sterile florets.*—Bud: Length: 0.5 cm. Diameter: 1.2 cm. Shape: Broad cup-shaped. Color: RHS 145C (Yellow-Green). Florets: Quantity of sterile flowers per panicle: 500. Aspect: Upright and outward to slightly drooping. Shape: Rotate. Diameter: 3.0 cm. Height: 0.8 cm. Lastingness on the plant: 6 weeks; flowers are persistent. Petals: Petals drop after the bud stage and never open; dropped petals are RHS NN155C (White) on the lower surface and RHS 73A (Red-Purple) on the upper surface. Sepals: Quantity per flower: Average of 4; occasionally 3 or 5. Arrangement: Rotate. Shape: Obovate to elliptic. Apex: Shallowly retuse to obtuse. Base: Cuneate. Margin: Entire. Length: 1.6 cm. Width: 1.1 cm. Appearance and texture (both upper and lower surfaces): Matte and glabrous. Color: Upper surface: RHS 145C (Yellow-Green) when opening and RHS 145B (Yellow-Green) when fully opened and fading to RHS 180B (Greyed-Purple) and RHS 180C (Greyed-Purple). Lower surface: RHS 145D (Yellow-Green) and a blend of RHS 145B (Yellow-Green) and 147D (Yellow-Green) when fully opened and fading to a blend of RHS 145B (Yellow-Green) and RHS 147D (Yellow-Green) and moderately flushed with RHS 181C (Greyed-Purple) and RHS 181D (Greyed-Purple). Pedicel: Length: 2.0 cm. Diameter: 1.0 mm. Angle: 45 degrees to the main peduncle. Strength: Moderately strong. Appearance and texture: Matte and sparsely covered with thin, adpressed hairs that are 0.4 mm in length and green-white (but too small to be accurately designated an RHS color). Color: RHS 157D (Green-White) and fading to RHS 157A (Green-White) towards the proximal end.

*Fertile florets.*—Bud: Length: 3.0 mm. Diameter: 3.0 mm. Shape: Broad obovate. Color: RHS 157A (Green-White) and tinged with RHS 75C (Purple); base (immature calyx) is RHS 145C (Yellow-Green). Quantity per panicle: Approximately 300. Aspect: Upright. Shape: Rotate; petals dropped when maturing. Diameter: 7.0 mm. Depth (height): 3.0 mm. Lastingness on the plant: 5 days and flowers are self-cleaning; flowers drop when mature. Petals: Quantity of petals per flower: 5. Arrangement: Rotate. Shape: Ovate; moderately concave. Apex: Acute. Base: Cuneate. Margin: Entire. Length: 3.0 mm. Width: 1.5 mm. Appearance and texture: Upper surface: Slightly glossy and glabrous. Lower surface: Matte and glabrous. Color: Upper surface: RHS NN155D (White) when opening and fully opened. Lower surface: RHS NN155C (White) and the top is tinged with RHS 75D (Purple) and RHS NN155D (White) when fully opened. Sepals: Quantity per flower: 5. Arrangement: Rotate. Shape: Deltoid. Apex: Broad acuminate. Base: Broad cuneate. Margin: Entire. Length: 1.0 mm. Width: 0.8 mm. Appearance and texture: Upper surface: Matte and glabrous. Lower surface: Glabrous and very slightly glossy. Color (both upper and lower surfaces): RHS 145C (Yellow-Green) when opening and fully opened. Pedicel: Length: 1.0 mm. Diameter: 0.5 mm. Angle: 20 degrees. Strength: Moderate. Texture and appearance: Moderately to densely covered with thin pubescence; average length is 0.3 mm and colored white to green-white (hairs are too small to be accurately measured with RHS designation); matte. Color: RHS 157D (Green-White).

Reproductive organs:

*Androecium.*—Sterile flowers located on the androecium but they drop after the bud stage and so no reproductive organs have been observed.

*Gynoecium.*—Fertile flowers located on the androecium. Quantity of stamen per flower: 10. Filament length: 3.0 mm. Filament color: RHS NN155D (White). Anther shape: Broad oblong. Anther length: 0.3 mm. Anther color: RHS 145B (Yellow-Green). Pollen quantity: Low to moderate. Pollen color: RHS 156B (Greyed-White). Quantity of pistils per flower: 3. Pistil length: 0.75 mm. Stigma shape: Club-shaped. Stigma color: RHS 157D (Green-White). Style length: 0.5 mm. Style color: RHS 145D (Yellow-Green). Ovary color: RHS 145B (Yellow-Green) to RHS 145D (Yellow-Green).

*Seed.*—Not observed to date.

COMPARISON WITH COMMERCIAL VARIETY

No comparison can be made with both parents of 'COUFLORI' as the parents are unknown and un-named.

'COUFLORI' can be distinguished between the commercial variety 'Limelight' (U.S. Plant Pat. No. 12,874) in Table 1.

TABLE 1

Comparison with Commercial Variety

| Characteristic | 'COUFLORI' | 'Limelight' |
|---|---|---|
| Height of plant | 86.0 cm | 180 cm to 240 cm |

I claim:

1. A new and distinct variety of *Hydrangea* plant designated 'COUFLORI' as illustrated and described herein.

* * * * *